US012642829B2

(12) United States Patent
Lin et al.

(10) Patent No.: US 12,642,829 B2
(45) Date of Patent: **\*Jun. 2, 2026**

(54) METHOD FOR ALLEVIATING OSTEOARTHRITIS

(71) Applicant: SYNBIO TECH INC., Kaohsiung City (TW)

(72) Inventors: Jin-Seng Lin, Tainan City (TW); Chia-Chia Lee, Kaohsiung City (TW); Ting-Yu Lee, Tainan City (TW); Han-Yin Hsu, Kaohsiung City (TW); Jiu-Yao Wang, Tainan City (TW)

(73) Assignee: SYNBIO TECH INC., Kaohsiung City (TW)

( \* ) Notice: Subject to any disclaimer, the term of this patent is extended or adjusted under 35 U.S.C. 154(b) by 434 days.

This patent is subject to a terminal disclaimer.

(21) Appl. No.: 18/318,531

(22) Filed: May 16, 2023

(65) Prior Publication Data

US 2024/0000870 A1 Jan. 4, 2024

Related U.S. Application Data

(63) Continuation-in-part of application No. 17/597,064, filed as application No. PCT/IB2021/059554 on Oct. 18, 2021, now Pat. No. 12,478,650.

(51) Int. Cl.
| | |
|---|---|
| *A61K 35/747* | (2015.01) |
| *A23L 33/135* | (2016.01) |
| *A61P 19/02* | (2006.01) |
| *C12N 1/205* | (2026.01) |
| *C12R 1/225* | (2006.01) |

(52) U.S. Cl.
CPC .......... *A61K 35/747* (2013.01); *A23L 33/135* (2016.08); *A61P 19/02* (2018.01); *C12N 1/205* (2021.05); *C12R 2001/225* (2021.05)

(58) Field of Classification Search
CPC ..... A61K 35/747; A23L 33/135; A61P 19/02; C12N 1/205; C12R 2001/225
See application file for complete search history.

(56) References Cited

U.S. PATENT DOCUMENTS

2010/0278795 A1\* 11/2010 Tategaki ................. A61P 37/00
435/252.9

OTHER PUBLICATIONS

Korotkyi et al. (Ukr Biochem J, 2019, 91:49) (Year: 2019).\*
NCBI Database Accession No. MN336189.1 (Aug. 26, 2019, 2 pages) (Year: 2019).\*

\* cited by examiner

*Primary Examiner* — David Steadman
*Assistant Examiner* — Joseph R Spangler
(74) *Attorney, Agent, or Firm* — HSML P.C.

(57) ABSTRACT

Disclosed herein is a method for alleviating osteoarthritis using a composition containing an isolated strain of *Lactobacillus delbrueckii* subsp. *lactis* LDL557 which is deposited at Deutsche Sammlung von Mikroorganismen and Zellkulturen GmbH under an accession number DSM 33617.

3 Claims, 7 Drawing Sheets
Specification includes a Sequence Listing.

SEQUENCE LISTING

```
Sequence total quantity: 3
SEQ ID NO: 1              moltype = DNA  length = 20
FEATURE                   Location/Qualifiers
misc_feature              1..20
                          note = Forward primer 27F for PCR amplification of
                           bacterial 16S rDNA fragment
source                    1..20
                          mol_type = other DNA
                          organism = synthetic construct
SEQUENCE: 1
agagtttgat cctggctcag                                           20

SEQ ID NO: 2              moltype = DNA  length = 18
FEATURE                   Location/Qualifiers
misc_feature              1..18
                          note = Reverse primer 1492R for PCR amplification of
                           bacterial 16S rDNA fragment
source                    1..18
                          mol_type = other DNA
                          organism = synthetic construct
SEQUENCE: 2
ggttaccttg ttacgact                                             18

SEQ ID NO: 3              moltype = DNA  length = 1523
FEATURE                   Location/Qualifiers
source                    1..1523
                          mol_type = genomic DNA
                          organism = Lactobacillus delbrueckii
                          sub_species = lactis
SEQUENCE: 3
tcaggacgaa cgctggcggc gtgcctaata catgcaagtc gagcgagctg aattcaaaga   60
tcccttcggg gtgatttgtt ggacgctagc ggcggatggg tgagtaacac gtgggcaatc  120
tgccctaaag actgggatac cacttggaaa caggtgctaa taccggataa caacatgaat  180
cgcatgattc aagtttgaaa ggcggcgcaa gctgtcactt taggatgagc ccgcggcgca  240
ttagctagtt ggtggggtaa aggcctacca aggcaatgat gcgtagccga gttgagagac  300
tgatcggcca cattgggact gagacacggc ccaaactcct acgggaggca gcagtaggga  360
atcttccaca atggacgcaa gtctgatgga gcaacgccgc gtgagtgaag aaggtcttcg  420
gatcgtaaag ctctgttgtt ggtgaagaag gatagaggca gtaactggtc tttatttgac  480
ggtaatcaac cagaaagtca cggctaacta cgtgccagca gccgcggtaa tacgtaggtg  540
gcaagcgttg tccggattta ttgggcgtaa agcgagcgca ggcggaatga taagtctgat  600
gtgaaagccc acggctcaac cgtggaactg catcggaaac tgtcattctt gagtgcagaa  660
gaggagagtg gaactccatg tgtagcggtg gaatgcgtag atatatggaa gaacaccagt  720
ggcgaaggcg gctctctggt ctgcaactga cgctgaggct cgaaagcatg ggtagcgaac  780
aggattagat accctggtag tccatgccgt aaacgatgag cgctaggtgt tggggacttt  840
ccggtcctca gtgccgcagc aaacgcatta agcgctccgc ctggggagta cgaccgcaag  900
gttgaaactc aaaggaattg acgggggccc gcacaagcgg tggagcatgt ggtttaattc  960
gaagcaacgc gaagaacctt accaggtctt gacatcctgc gctacaccta gagataggtg 1020
gttcccttcg gggacgcaga gacaggtggt gcatggctgt cgtcagctcg tgtcgtgaga 1080
tgttgggtta agtcccgcaa cgagcgcaac ccttgtcttt agttgccatc attaagttgg 1140
```

-continued

```
gcactctaaa gagactgccg gtgacaaacc ggaggaaggt ggggatgacg tcaagtcatc  1200
atgcccctta tgacctgggc tacacacgtg ctacaatggg cagtacaacg agaagcaaac  1260
ccgcgagggt aagcggatct cttaaagctg ctctcagttc ggactgcagg ctgcaactcg  1320
cctgcacgaa gctggaatcg ctagtaatcg cggatcagca cgccgcggtg aatacgttcc  1380
cgggccttgt acacaccgcc cgtcacacca tggaagtctg caatgcccaa agtcggtgag  1440
ataaccttta taggagtcag ccgcctaagg cagggcagat gactggggtg aagtcgtaac  1500
aaggtagccg taggagaacc tgc                                          1523
```

METHOD FOR ALLEVIATING OSTEOARTHRITIS

CROSS-REFERENCE TO RELATED APPLICATION

This application is a continuation-in-part application of U.S. patent application Ser. No. 17/597,064 (filed on Dec. 23, 2021), which is a national stage entry of PCT/IB2021/059554 (filed on Oct. 18, 2021) that claims priority of Taiwanese Patent Application No. 110110252 (filed on Mar. 22, 2021). This application claims the benefits and priority of all these prior applications and incorporates by reference the contents of these prior applications in their entirety.

SEQUENCE LISTING XML

The Sequence Listing submitted concurrently herewith with a file name of "PE-67957-AM-SEQUENCE LISTING.xml," a creation date of May 9, 2023, and a size of 5710 bytes, is part of the specification and is incorporated by reference in its entirety.

FIELD

The present disclosure relates to a method for alleviating osteoarthritis using a composition including an isolated strain of *Lactobacillus delbrueckii* subsp. *lactis* LDL557.

BACKGROUND

Osteoarthritis (OA) is a degenerative joint disease affecting hand, hip, and knee joints. The incidence of OA increases with age, and is the main cause of joint disability in the elderly population. Besides ageing, a number of risk factors may also predispose a subject to develop OA, including menopause, joint injury or overuse, low bone density, muscle weakness, and joint laxity. Osteoarthritis might cause joint inflammation, swelling, deformity, pain, atrophy, stiffness, and eventually, impaired mobility.

Currently, drugs used clinically to alleviate osteoarthritis include non-steroidal anti-inflammatory drugs (such as flurbiprofen and loxoprofen), anti-inflammatory drugs (such as corticosteroids), and chondroprotective agents. However, these drugs might not be able to achieve the desired therapeutic effect and might also cause severe side effects.

Probiotics are resident normal flora of the intestinal tract, and are believed to play important roles in regulating proper intestinal immunity and digestion by balancing intestinal microflora. These beneficial microorganisms are widely used as live microbial dietary supplements and can help to restore intestinal microfloral balance. Many species of lactic acid bacteria (LAB) are conferred with the generally recognized as safe (GRAS) status, and are widely used as probiotics.

Common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc. LAB have been shown to be capable of inhibiting the growth of pathogenic bacteria in the gastrointestinal tract and alleviating lactose intolerance, and to have anti-cancer, anti-bacterial, anti-fatigue, and blood pressure lowering effects.

Previous studies demonstrated that certain strains of LAB are effective in alleviating various inflammation-related disorders. For example, it has been reported in Bonato A. et al. (2022), *Osteoarthritis and Cartilage,* 30(6):786-801 that the administration of probiotics such as *Lactobacillus casei* Shirota, *Lactobacillus paracasei* M5, *Streptococcus thermophiles*, and *Bifidobacterium longum* can effectively alleviate OA symptoms.

In spite of the aforesaid, there is still a need to develop a new strategy that can be utilized for alleviating osteoarthritis.

SUMMARY

Therefore, an object of the present disclosure is to provide a method for alleviating osteoarthritis, which can alleviate at least one of the drawbacks of the prior art, and which includes administering to a subject in need thereof a composition including an isolated strain of *Lactobacillus delbrueckii* subsp. *lactis* LDL557.

The isolated strain of *Lactobacillus delbrueckii* subsp. *lactis* LDL557 is deposited at Deutsche Sammlung von Mikroorganismen and Zellkulturen GmbH under an accession number DSM 33617.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
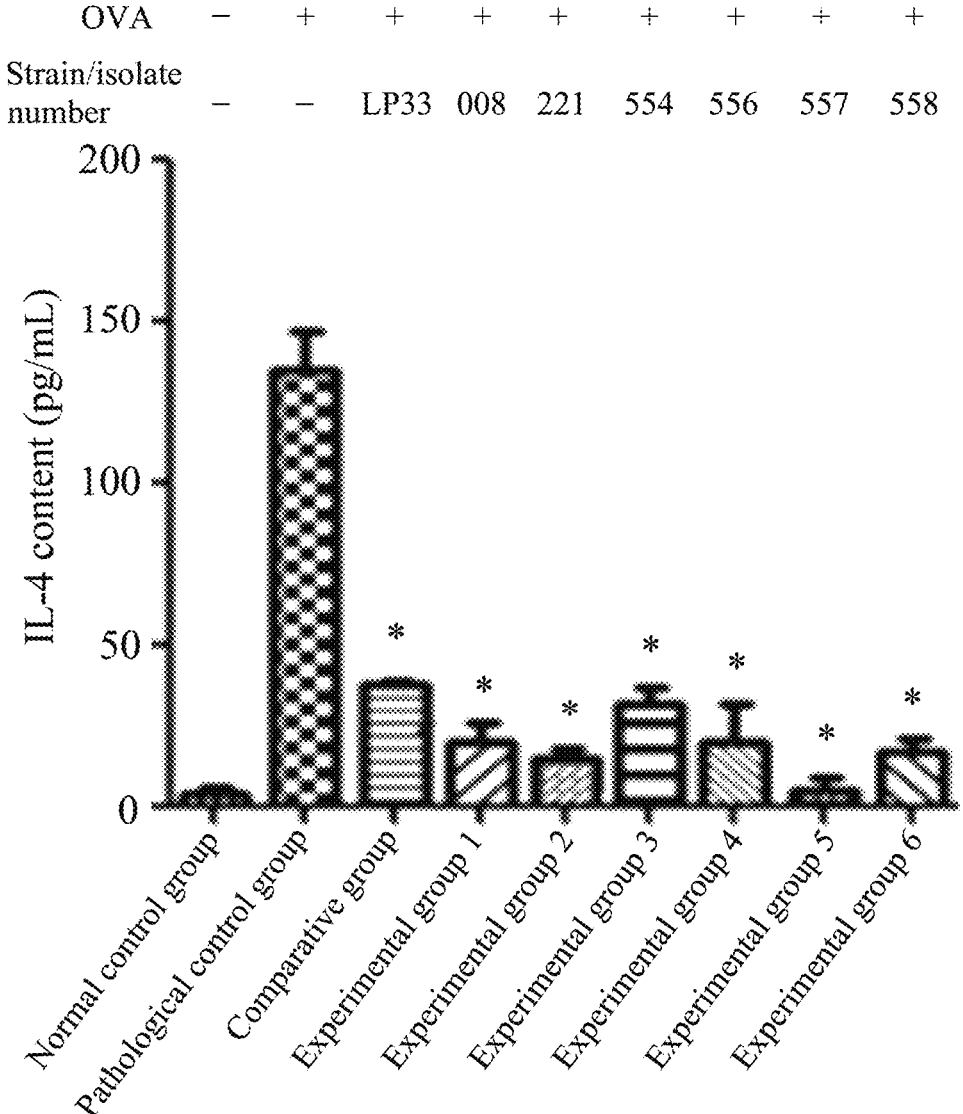
FIG. 1 shows the interleukin-4 (IL-4) content in each group of Example 2, infra, in which the symbol "*" represents $p < 0.05$ (compared with the pathological control group).
Figure 2:
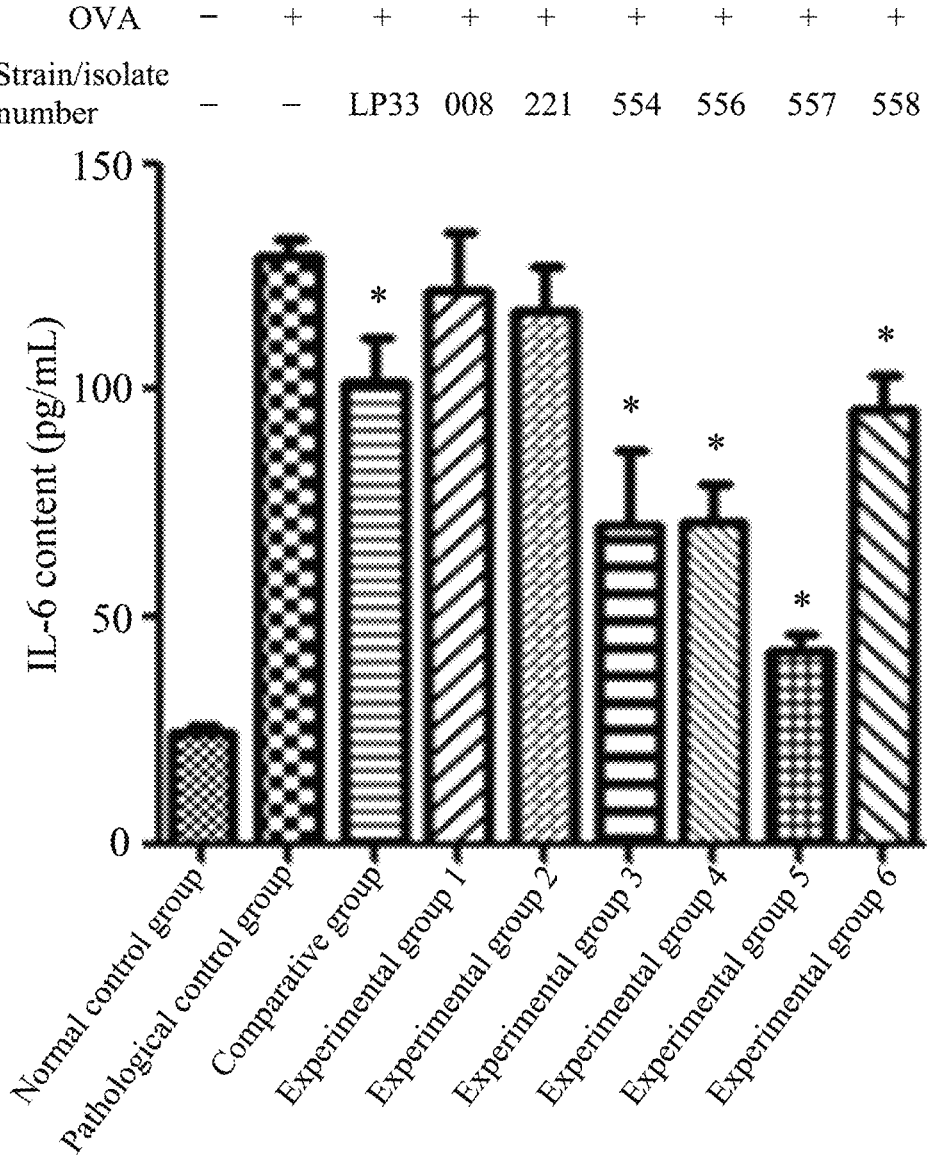
FIG. 2 shows the IL-6 content in each group of Example 2, infra, in which the symbol "*" represents $p < 0.05$ (compared with the pathological control group).
Figure 3:
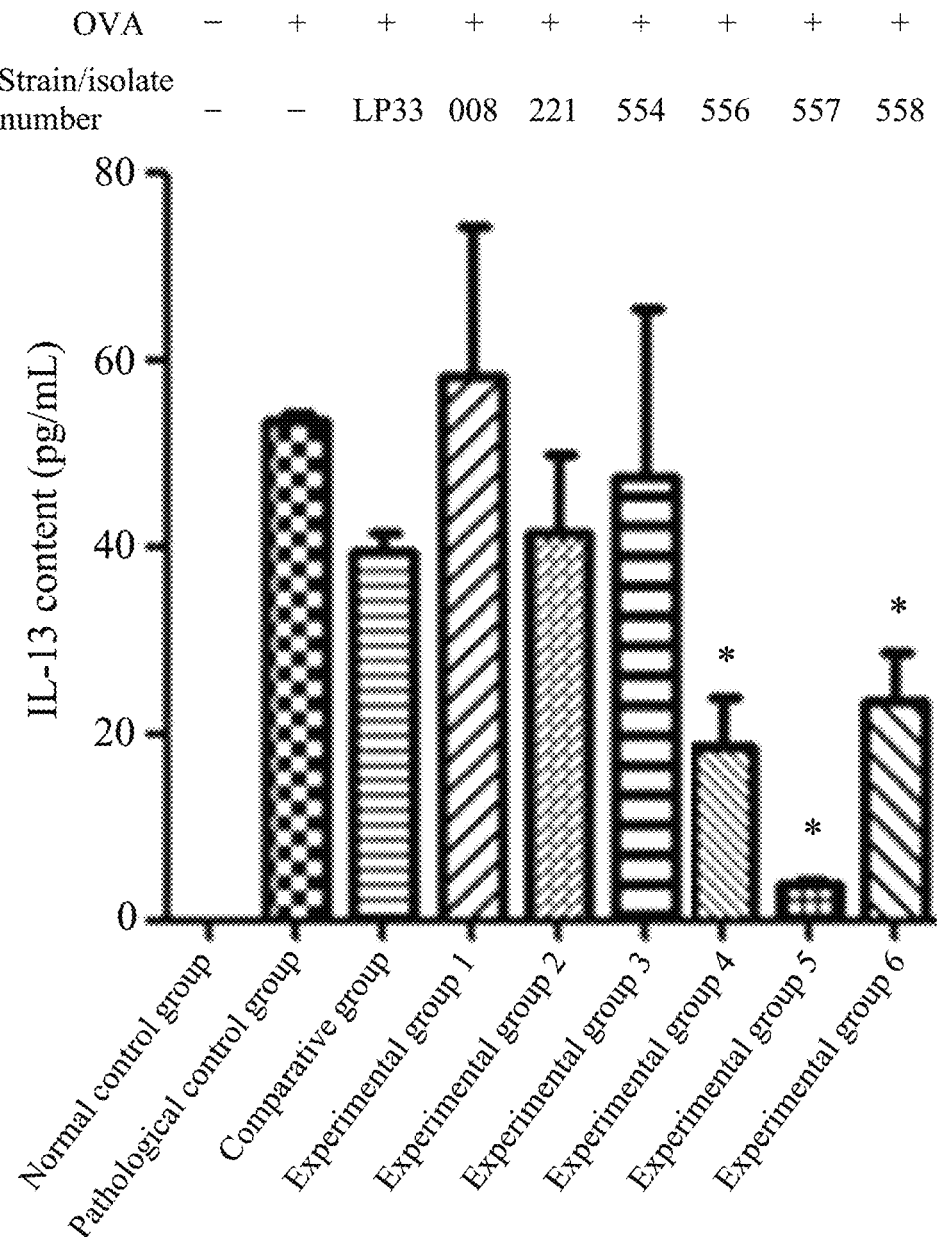
FIG. 3 shows the IL-13 content in each group of Example 2, infra, in which the symbol "*" represents $p < 0.05$ (compared with the pathological control group).
Figure 4:
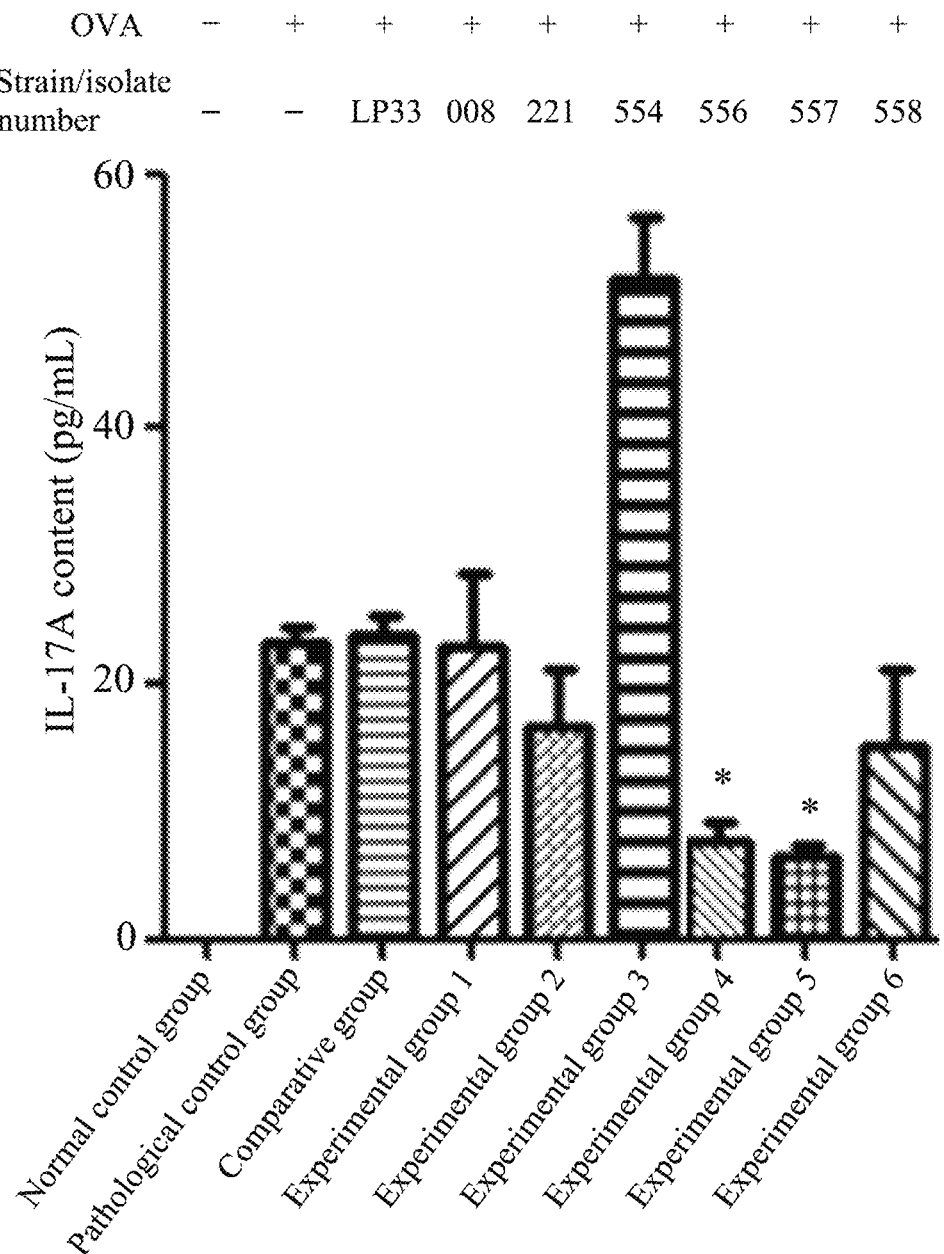
FIG. 4 shows the IL-17A content in each group of Example 2, infra, in which the symbol "*" represents $p < 0.05$ (compared with the pathological control group).

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method for alleviating osteoarthritis, which includes administering to a subject in need thereof a composition including an isolated strain of *Lactobacillus delbrueckii* subsp. *lactis* LDL557.

The isolated strain of *Lactobacillus delbrueckii* subsp. *lactis* LDL557 is deposited at Deutsche Sammlung von Mikroorganismen and Zellkulturen GmbH under an accession number DSM 33617.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administration" or "administering" means introducing, providing or delivering a pre-determined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

In certain embodiments, the composition of the present disclosure may be formulated as a food product using a standard technique well known to one of ordinary skill in the art. For example, the composition may be directly added to an edible material or may be used to prepare an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, butter, beverages (e.g., tea and coffee), functional beverages, flour products, baked foods, confectionery, candies, health foods, animal feeds, and dietary supplements.

In addition, the composition of the present disclosure may be prepared in the form of a pharmaceutical composition.

According to the present disclosure, the pharmaceutical composition may be formulated into a suitable dosage form for parenteral, oral, topical or inhalation administration (i.e., respiratory tract administration) using technology well known to those skilled in the art. The suitable dosage form includes, but is not limited to, injections (e.g., sterile aqueous solutions or dispersions), sterile powder, tablets, troches, lozenges, pellets, capsules, dispersible powder or granules, solutions, suspensions, emulsions, drops, syrup, elixirs, slurry, sprays (e.g., nasal sprays or oral sprays), external preparations (e.g., ointments, creams, lotions, gels, and foams), and the like.

According to the present disclosure, the pharmaceutical composition may be administered by parenteral routes selected from the group consisting of intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration.

According to the present disclosure, the pharmaceutical composition may be administered by inhalation routes selected from the group consisting of oral inhalation and nasal inhalation. In certain embodiments, the pharmaceutical composition may be formulated into a suitable dosage form for nasal inhalation.

The pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, anti-caking agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The dose and frequency of administration of the pharmaceutical composition may vary depending on the following factors: the severity of the illness or disorder to be treated, routes of administration, and age, physical condition and response of the subject to be treated. In general, the pharmaceutical composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials

1. BD DIFCO™ MRS (De Man, Rogosa and Sharpe) broth medium (Cat. No. 288130) used in the following experiments was purchased from Creative Life Science Co., Ltd., Taiwan.

2. MRS agar medium used in the following experiments was prepared by adding 1.5% agar to MRS broth medium.

3. Preparation of human peripheral blood mononuclear cells (human PBMCs)

Blood samples were collected from healthy human volunteers, and an acid citrate dextrose (ACD) solution was used as an anticoagulant. The blood samples were subjected to density gradient centrifugation (900 g, 30 minutes) at 4° C. with SIGMA-ALDRICH® density gradient cell separation (i.e., Histopaque®-1077) (Cat. No. 10771). Thereafter, the lymphocyte layer was harvested, followed by adding a red blood cell (RBC) lysis buffer. After centrifugation at 2000 rpm and 4° C. for 10 minutes, the RBC debris was removed, so as to obtain human PBMCs, and the cell concentration was adjusted to $2\times10^6$ cells/mL using a GIBCO™ RPMI 1640 medium containing 10% fetal bovine serum (FBS).

4. Preparation of ovalbumin (OVA) emulsion

20 µg of SIGMA-ALDRICH® OVA (Cat. No. A5503) was dissolved in 200 µL of a THERMO FISHER SCIENTIFIC aluminum hydroxide suspension i.e., Imject™ Alum adjuvant) (Cat. No. 77161), so as to prepare an OVA emulsion.

5. Preparation of monosodium iodoacetate (MIA) solution 1 mg of SIGMA-ALDRICH® monosodium iodoacetate (MIA) (Cat. No. 19148) was dissolved in 20 μL of a 0.9% sodium chloride (NaCl) solution, so as to prepare a MIA solution.

6. Experimental mice

Female BALB/c mice used in the following experiments were purchased from BioLasco Taiwan Co., Ltd. All the experimental animals were housed in an animal room under the following laboratory conditions: an alternating 12-hour light and 12-hour dark cycle, a temperature maintained at 22° C. to 25° C., and a relative humidity maintained at 40% to 60%. Furthermore, water and feed were provided ad libitum for all the experimental animals. All experiments on animals were approved by the Experimental Ethics Committee of the Livestock Research Institute of the Council of Agriculture, Taiwan, and were conducted according to the Guide for the Care and Use of Laboratory Animals of National Institute of Health (NIH).

7. Experimental rats

Male Sprague Dawley rats (6 weeks old, with a body weight of approximately 151 to 170 g) used in the following experiments were purchased from BioLasco Taiwan Co., Ltd. All the experimental rats were housed in an animal room under the following laboratory conditions: an alternating 12-hour light and 12-hour dark cycle, a temperature maintained at 22° C. to 26° C., and a relative humidity maintained at 40% to 70%. Furthermore, water and feed were provided ad libitum for all the experimental rats. All experimental procedures involving the experimental rats were in compliance with the legal provision of the Institutional Animal Care and Use Committee of Kaohsiung Medical University, Taiwan, and were carried out according to the Guide for the Care and Use of Laboratory Animals of National Institutes of Health (NIH).

General Procedures

1. Statistical Analysis

All the experiments described below were performed in triplicates. The experimental data of all the test groups are expressed as mean±standard deviation (SD). Statistical analysis was conducted using GRAPHPAD PRISM® Software 7.04 (GraphPad Software Inc., San Diego, USA). All of the experimental data were analyzed using one-way analysis of variance (ANOVA) followed by Dunnett's post-hoc test, so as to evaluate the differences between the groups. Statistical significance is indicated by p<0.05.

Example 1. Preliminary Screening of Lactic Acid Bacteria (LAB) Isolates Having Anti-Inflammatory Activity A. Source and Isolation of Tested Strains Corn silage purchased from Taiwan Dairy Farm (Tainan, Taiwan) was used as a sample source. First, the corn silage was mixed with a 0.85% saline solution, followed by homogenization with a homogenizer (Oster 6642). The resultant homogenized mixture was subjected to serial dilution with a 0.85% saline solution, so as to obtain six dilutions (prepared using dilution factors of $10^2$, $10^3$, $10^4$, $10^5$, $10^6$, and $10^7$). 0.1 mL of a respective one of the six dilutions was evenly spread onto MRS agar medium, and was then cultured at 37° C. for 48 hours.

Fifteen LAB isolates were randomly selected from the MRS agar medium, and were designated as 008, 384, 221, 542, 544, 548, 553, 554, 555, 556, 557, 558, 561, 564, and 565, respectively. These isolates were subjected to the following analyses.

B. Preparation of Heat-Killed Bacterial Suspension of LAB Isolate

A respective one of the fifteen LAB isolates obtained in section A of this example was inoculated in an amount of 1% (v/v) into 9 mL of MRS broth medium, and was then cultured at 37° C. for 16 hours to 18 hours. After centrifugation at 3,500 rpm for 10 minutes, the resultant cell pellet was collected, and was washed with phosphate-buffered saline (PBS), followed by suspending in PBS, so as to obtain a bacterial suspension having a bacterial concentration of $10^9$ CFU/mL. The respective resultant bacterial suspension was subjected to a heat-killing treatment at 100° C. for 30 minutes, thereby obtaining a heat-killed bacterial suspension. The fifteen heat-killed bacterial suspensions thus obtained were used for the following experiment.

C. Screening of LAB Isolates Able to Stimulate Secretion of Interleukin-10 (IL-10) and Interferon-γ (IFN-γ) by Human PBMCs The human PBMCs prepared in section 3 of "General Experimental Materials" were divided into 16 groups, including one control group and fifteen experimental groups (i.e., experimental groups 1 to 15). Each group of the human PBMCs was incubated in a respective well of a 24-well culture plate containing 1 mL of an RPMI 1640 medium (supplemented with 10% FBS) at $2 \times 10^6$ cells/well, followed by cultivation in an incubator (37° C., 5% $CO_2$) for 24 hours. Afterwards, each of the cell cultures of the fifteen experimental groups was treated with 100 μL of the respective heat-killed bacterial suspension prepared in section B of this example. The cell culture of the control group received no treatment.

After cultivation in an incubator (37° C., 5% $CO_2$) for 24 hours, the respective resultant cell culture was subjected to centrifugation at 3,000 rpm for 15 minutes. The resultant supernatant was collected, and was then subjected to determination of IL-10 and IFN-γ contents using an EBIOSCIENCE™ IFN-γ enzyme-linked immunosorbent assay (ELISA) kit (Cat. No. 88-7316) and an EBIOSCIENCE™ IL-10 ELISA kit (Cat. No. 88-7106) in accordance with the manufacturer's instructions.

As shown in Table 1 below, the IFN-γ contents determined in the experimental groups 1, 3, 8, and 11 to 12 were each not lower than 3,000 pg/mL, and the IFN-γ and IL-10 contents determined in the experimental group 10 were not lower than 1,000 pg/mL. According to these results, the Applicant selected LAB isolates 008, 221, 554, 556, 557, and 558 for further experimentation to evaluate the anti-allergic activities of these strains.

TABLE 1

| Group | Strain number of LAB isolate | IFN-γ content (pg/mL) | IL-10 content (pg/mL) |
|---|---|---|---|
| Control group | — | 6 ± 1 | 35 ± 6 |
| Experimental group 1 | 008 | 5832 ± 118 | 198 ± 1 |
| Experimental group 2 | 384 | 1705 ± 277 | 261 ± 4 |
| Experimental group 3 | 221 | 3219 ± 227 | 640 ± 35 |
| Experimental group 4 | 542 | 2606 ± 126 | 575 ± 58 |

TABLE 1-continued

| Group | Strain number of LAB isolate | IFN-γ content (pg/mL) | IL-10 content (pg/mL) |
|---|---|---|---|
| Experimental group 5 | 544 | 1773 ± 10 | 596 ± 22 |
| Experimental group 6 | 548 | 490 ± 150 | 1243 ± 2 |
| Experimental group 7 | 553 | 2444 ± 363 | 444 ± 26 |
| Experimental group 8 | 554 | 4596 ± 210 | 564 ± 20 |
| Experimental group 9 | 555 | 2445 ± 125 | 343 ± 12 |
| Experimental group 10 | 556 | 1080 ± 17 | 1587 ± 111 |
| Experimental group 11 | 557 | 3392 ± 407 | 1209 ± 116 |
| Experimental group 12 | 558 | 4349 ± 276 | 262 ± 8 |
| Experimental group 13 | 561 | 1503 ± 52 | 622 ± 2 |
| Experimental group 14 | 564 | 2796 ± 101 | 428 ± 3 |
| Experimental group 15 | 565 | 2168 ± 82 | 829 ± 24 |

Example 2. Screening of LAB Isolates Having in Vitro Anti-Allergic Activity

Materials:

A. Preparation of Heat-Killed Bacterial Suspension of *Lactobacillus paracasei* 33 (LP33)

A heat-killed bacterial suspension of *Lactobacillus paracasei* 33 (having a bacterial concentration of $10^9$ CFU/mL) was prepared according to the procedures described in the abovementioned section B of Example 1.

Methods:

The in vitro anti-allergic activity was analyzed using a method slightly modified from that described by Lee J. et al. (2013), *J. Microbiol. Biotechnol.*, 23:724-730. Briefly, the female BALB/c mice were divided into nine groups, including a normal control group, a pathological control group, a comparative group, and six experimental groups (i.e., experimental groups 1 to 6)(n=12 per group). The mice of the pathological control group, comparative group, and six experimental groups were intraperitoneally injected with the OVA emulsion prepared in section 4 of "General Experimental Materials" at a dose of 200 μL/mouse. The mice of the normal control group were intraperitoneally injected with PBS at a dose of 200 μL/mouse. The mice in each group was subjected to the once-a-week injection for a total period of 2 weeks.

After the 2-week experimental period, the mice in each group were anesthetized using $CO_2$, and were subsequently sacrificed. Thereafter, the spleen tissue was obtained from each mouse carcass, followed by grinding. Each group of the resultant milled spleen sample was incubated in a respective well of a 24-well culture plate containing a suitable amount of an RPMI 1640 medium (supplemented with 10% FBS), followed by cultivation in an incubator (37° C., 5% $CO_2$) for 24 hours.

Subsequently, each group of the spleen cells thus obtained was incubated in a respective well of a 24-well culture plate containing 1 mL of an RPMI 1640 medium (supplemented with 10% FBS and 100 μg/mL OVA) at $2 \times 10^6$ cells/well, followed by cultivation in an incubator (37° C., 5% $CO_2$) for 48 hours. Afterwards, each of the cell cultures of the experimental groups 1 to 6 was added with 100 μL of a respective one of the heat-killed bacterial suspensions of LAB isolates 008, 221, 554, 556, 557, and 558 prepared in the abovementioned section B of Example 1. In addition, the cell culture of the comparative group was added with 100 μL of the heat-killed bacterial suspension of *Lactobacillus paracasei* 33, and the cell cultures of the normal control group and pathological control group received no treatment.

The treating agents for all the groups are summarized in Table 2 below.

TABLE 2

| Group | Treating agent |
|---|---|
| Normal control group | — |
| Pathological control group | — |
| Comparative group | Heat-killed bacterial suspension of *Lactobacillus paracasei* 33 |
| Experimental group 1 | Heat-killed bacterial suspension of LAB isolate 008 |
| Experimental group 2 | Heat-killed bacterial suspension of LAB isolate 221 |
| Experimental group 3 | Heat-killed bacterial suspension of LAB isolate 554 |
| Experimental group 4 | Heat-killed bacterial suspension of LAB isolate 556 |
| Experimental group 5 | Heat-killed bacterial suspension of LAB isolate 557 |
| Experimental group 6 | Heat-killed bacterial suspension of LAB isolate 558 |

Each group was cultivated in an incubator (37° C., 5% $CO_2$) for 48 hours. After centrifugation at 3,000 rpm for 15 minutes, the resultant supernatant was collected, and was subjected to determination of IL-4, IL-6, IL-13, and IL-17A contents using an INVITROGEN™ IL-4 ELISA kit (Cat. No. BMS613TEN), an INVITROGEN™ IL-6 ELISA kit (Cat. No. 88-7064-88), an INVITROGEN™ IL-13 ELISA kit (Cat. No. 88-7137-86), and an INVITROGEN™ IL-17A ELISA kit (Cat. No. BMS6001TEN) in accordance with the manufacturer's instructions.

The data thus obtained were analyzed according to the method described in section 1 of "General Procedures".

Results:

Referring to FIGS. 1 to 4, the contents of IL-4, IL-6, IL-13, and IL-17A determined in the experimental group 5 were apparently or significantly lower than those determined in the experimental groups 1 to 4 and 6, the comparative group, and the pathological control group, indicating that LAB isolate 557 had the best in vitro anti-allergic activity.

Therefore, LAB isolate 557 showed more potential for development, and was subjected to characteristic analysis described below.

Example 3. Characteristic Analysis of LAB Isolate 557

In order to identify the bacterial species of LAB isolate 557, the following preliminary characteristic determination, 16S rDNA sequence analysis, and carbohydrate fermentation profiling were conducted.

A. Preliminary Tests

Items of the preliminary tests conducted for LAB isolate 557 include: gram staining, morphological observation, mobility, catalase test, growth under aerobic and anaerobic conditions, and ability to produce an endospore.

The results of the aforesaid preliminary tests indicate that LAB isolate 557 is gram-positive, non-motile, catalase-negative, grows under anaerobic conditions, and non-endospore forming.

B. 16S rDNA Sequence Analysis

Genomic DNA of LAB isolate 557 was extracted using Genomic DNA Mini Kit (Geneaid Biotech Ltd., Cat. No. GB300). The thus obtained genomic DNA was used as a template and was subjected to polymerase chain reaction (PCR) that was performed using a designed primer pair specific for 16S ribosomal DNA (rDNA) and the reaction conditions shown in Table 3, thereby obtaining a PCR product having a size of approximately 474 bp.

TABLE 3

| | Contents | Volume (μL) |
|---|---|---|
| Genomic DNA of LAB isolate 557 (10 ng) | | 1 |
| 16S rDNA-specific primer pair | Forward primer 27F (10 μM): 5'-agagtttgatcctggctcag-3' (SEQ ID No: 1) | 0.5 |
| | Reverse primer 1492R (10 μM): 5'-ggttaccttgttacgact-3' (SEQ ID No: 2) | 0.5 |
| | dNTPs (10 mM) | 0.5 |
| | 10X buffer | 2.5 |
| | Tag DNA polymerase (5 U/μL) | 0.5 |
| | ddH₂O | 18.5 |

Operation conditions: denaturation at 94° C. for 5 min, followed by 30 cycles of the following reactions: denaturation at 95° C. for 60 sec, primer annealing at 50° C. for 60 sec, and extension at 72° C. for 60 sec; and lastly, elongation at 72° C. for 8 min.

The resultant PCR product was subjected to 2% agarose gel electrophoresis analysis for molecular weight verification.

Thereafter, the PCR product was verified by sequencing analysis which was entrusted to Genomics BioSci & Tech Co., Ltd., Taiwan, so as to obtain the 16S rDNA sequence (SEQ ID No: 3) of LAB isolate 557. Through comparison with the data in the NCBI's gene database, it was found that the 16S rDNA sequence of LAB isolate 557 is most homologous to that of *Lactobacillus delbrueckii* subsp. *lactis.*

In view of the aforesaid experimental results, LAB isolate 557 of the present disclosure is identified as *Lactobacillus delbrueckii* subsp. *lactis.* In order to confirm whether *Lactobacillus delbrueckii* subsp. *lactis* strain LDL557 (i.e. LAB isolate 557) is a novel *Lactobacillus delbrueckii* subsp. *lactis* strain, the following experiment was conducted.

C. Carbohydrate Fermentation Profiling

The carbohydrate fermentation profile of *Lactobacillus delbrueckii* subsp. *lactis* strain LDL557 was determined using a BIOMÉRIEUX API (analytical profile index) test strip (i.e., API® 50 CHL identification system. The result is shown in Table 4 below.

TABLE 4

| Carbohydrate | Capability of fermenting carbohydrate tested to produce acid |
|---|---|
| Glycerol | – |
| Erythritol | – |
| D-Arabinose | – |
| L-Arabinose | – |
| D-Ribose | – |
| D-Xylose | – |
| L-Xylose | – |
| D-Adonitol | – |
| Methyl-β-D-xylopyranoside | – |
| D-Galactose | – |
| D-Glucose | + |
| D-Fructose | + |
| D-Mannose | – |
| L-Sorbose | – |
| L-Rhamnose | – |

TABLE 4-continued

| Carbohydrate | Capability of fermenting carbohydrate tested to produce acid |
|---|---|
| Dulcitol | – |
| Inositol | – |
| D-Mannitol | – |
| D-Sorbitol | – |
| Methyl-α-D-mannopyranoside | – |
| Methyl-α-D-glucopyranoside | – |
| N-Acetylglucosamine | + |
| Amygdalin | – |
| Arbutin | – |
| Esculin | – |
| Salicin | – |
| D-Lactose | + |
| D-Melibiose | – |
| D-Saccharose | + |
| D-Trehalose | + |
| Inulin | – |
| D-Melezitose | – |
| D-Raffinose | – |
| Amidon | – |
| Glycogen | – |
| Xylitol | – |
| Gentiobiose | – |
| D-Turanose | – |
| D-Lyxose | – |
| D-Tagatose | – |
| D-Fucose | – |
| L-Fucose | – |
| D-Arabitol | – |
| L-Arabitol | – |
| Gluconate | – |
| 2-Ketogluconate | – |
| 5-Ketogluconate | – |

Note:
"+" indicates that *Lactobacillus delbrueckii* subsp. *lactis* strain LDL557 is capable of fermenting the carbohydrate tested to produce an acid, whereas "–" indicates that the strain has no such capability.

The aforesaid result was subjected to comparison with the data in the APIWEB™ on-line bacteria and yeast database, and it was found that the carbohydrate fermentation profile of *Lactobacillus delbrueckii* subsp. *lactis* strain LDL557 of the present disclosure has 84.9% identity to that of *Lactobacillus delbrueckii* subsp. *lactis*, suggesting that the *Lactobacillus delbrueckii* subsp. *lactis* strain LDL557 characterized thus far by the applicant is different from conventionally known strains of *Lactobacillus delbrueckii* subsp. *lactis.*

Based on the aforementioned characterization results, the applicant believes that the *Lactobacillus delbrueckii* subsp. *lactis* strain LDL557 is a novel strain of *Lactobacillus delbrueckii* subsp. *lactis.* As such, *Lactobacillus delbrueckii* subsp. *lactis* strain LDL557 has been deposited at the Biosource Collection and Research Center (BCRC) of the Food Industry Research and Development Institute (FIRDI), Taiwan under an accession number BCRC 910780 since May 17, 2017, and has also been deposited at the Deutsche Sammlung von Mikroorganismen and Zellkulturen (DSMZ) GmbH under an accession number DSM 33617 since Aug. 10, 2020 in accordance with the Budapest Treaty.

Example 4. Evaluation for the Effect of *Lactobacillus delbrueckii* subsp. *lactis* LDL557 in Alleviating Osteoarthritis (OA)

A. Preparation of Bacterial Suspension of *Lactobacillus delbrueckii* subsp. *lactis* LDL557

*Lactobacillus delbrueckii* subsp. *lactis* LDL557 was inoculated in MRS broth, and was then cultured at 37° C. for 16 hours to 18 hours. After centrifugation at 5,000 rpm and 4° C. for 10 minutes, the resultant cell pellet was collected, and was washed with phosphate-buffered saline (PBS), followed by a freeze-drying treatment, so as to obtain a freeze-dried powder of *Lactobacillus delbrueckii* subsp. *lactis* LDL557.

The freeze-dried powder of *Lactobacillus delbrueckii* subsp. *lactis* LDL557 was mixed with a suitable amount of a 0.85% physiological salt solution, so as to obtain a bacterial suspension having a bacterial concentration of $10^9$ CFU/mL. The resultant bacterial suspension was used for the following experiments.

B. Preparation of Heat-Killed Bacterial Suspension of *Lactobacillus delbrueckii* subsp. *lactis* LDL557

*Lactobacillus delbrueckii* subsp. *lactis* LDL557 was subjected to the procedures described in the abovementioned section B of Example 1, so as to obtain a heat-killed bacterial suspension having a bacterial concentration of $10^8$ CFU/mL. The resultant heat-killed bacterial suspension was used for the following experiments.

C. Induction of OA and Administration of *Lactobacillus delbrueckii* subsp. *lactis* LDL557

The Sprague Dawley rats were divided into seven groups, including one normal control group, one pathological control group, one comparative group, and four experimental groups (i.e., experimental groups 1 to 4) (n=8 rats in each group). The rats of the experimental groups 1 and 2 were orally administered with the bacterial suspension of *Lactobacillus delbrueckii* subsp. *lactis* LDL557 prepared in section A of this example, the rats of the experimental groups 3 and 4 were orally administered with the heat-killed bacterial suspension of *Lactobacillus delbrueckii* subsp. *lactis* LDL557 prepared in section B of this example, and the rats of the comparative group were orally administered with UC-II® undenatured type II collagen powder (InterHealth Nutraceuticals Inc.). In addition, each of the rats of the normal control group and pathological control group was orally administered with a maltodextrin solution (Cargill). Each rat was subjected to the administration once daily for a 8-week treatment period.

The treating agent and the dosage thereof for each group are summarized in Table 5 below.

TABLE 5

| Group | Treating agent | Dosage |
|---|---|---|
| Normal control group | Maltodextrin solution | 1 ml/kg |
| Pathological control group | Maltodextrin solution | 1 ml/kg |
| Comparative group | UC-II ® undenatured type II collagen powder | 4.11 mg/kg |
| Experimental group 1 | Bacterial suspension of *Lactobacillus delbrueckii* subsp. *lactis* LDL557 | $1.03 \times 10^9$ CFU/kg |
| Experimental group 2 | Bacterial suspension of *Lactobacillus delbrueckii* subsp. *lactis* LDL557 | $5.14 \times 10^9$ CFU/kg |
| Experimental group 3 | Heat-killed bacterial suspension of *Lactobacillus delbrueckii* subsp. *lactis* LDL557 | $1.03 \times 10^9$ CFU/kg |
| Experimental group 4 | Heat-killed bacterial suspension of *Lactobacillus delbrueckii* subsp. *lactis* LDL557 | $5.14 \times 10^9$ CFU/kg |

On the $3^{rd}$ week after the administration of the treating agent, 20 µL of the MIA solution prepared in section 5 of "General Experimental Materials" was injected subcutaneously into the knee joint cavity of the left hindlimb of the respective one of the rats of the pathological control group, the comparative group and four experimental groups, so as to induce the occurrence of osteoarthritis. In addition, the rats of the normal control group were injected with 20 µL of a 0.9% saline solution.

D. Determination of Knee Joint Diameter

After the 8-week experimental period, the knee joint of the left hindlimb of each rat was subjected to determination of diameter using an electronic digital caliper.

The data thus obtained were analyzed according to the method described in section 1 of "General Procedures".

Figure 5:
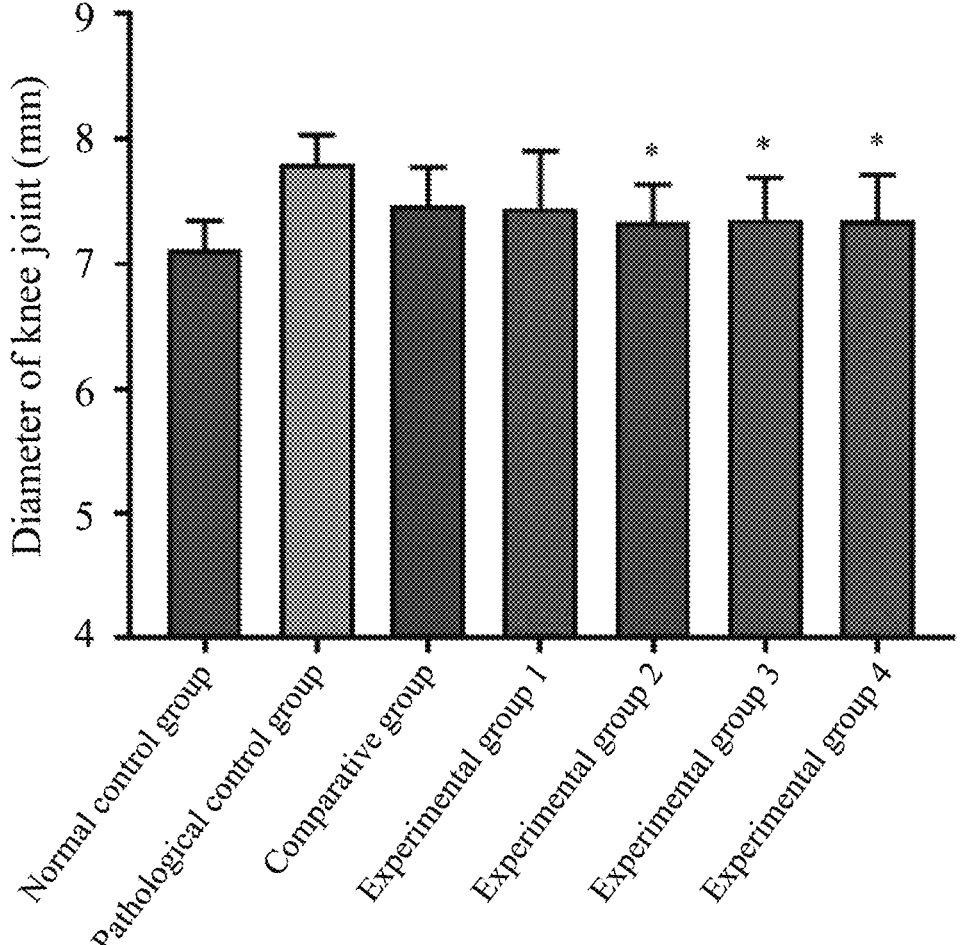
FIG. 5 shows the diameter of the knee joint determined in each group of Example 4, infra, in which the symbol "*" represents $p < 0.05$ (compared with the pathological control group).

Referring to FIG. 5, the diameters of the knee joints determined in the experimental groups 1 to 4 were each less than that determined in the pathological control group. The results indicate that *Lactobacillus delbrueckii* subsp. *lactis* LDL557 of the present disclosure, whether in the form of live cells or dead cells, can effectively alleviate swelling and enlargement in the knee joint.

E. Preparation of Biological Sample

After completion of the determination of knee joint diameter as described in section D of this example, the respective rat was sacrificed by virtue of isoflurane, and the cartilage tissue was obtained from the left knee joint of the respective rat carcass. Next, the cartilage tissue was fixed with a 10% SIGMA-ALDRICH® neutral buffered formalin (Cat. No. F8775) at room temperature for 48 hours, and was then decalcified with a 10% formic acid solution. The decalcified tissue sample was then embedded with an optimal cutting temperature (OCT) compound (Cat. No. 4853, Sakura Finetek USA), followed by slicing to obtain a tissue section having a thickness ranging from 5 µm to 10 µm.

F. Hematoxylin-Eosin (H&E) Staining

The tissue section obtained in section E of this example was subjected to hematoxylin-eosin staining using a staining protocol well-known to those skilled in the art, and was then observed under an optical microscope (Olympus, CKX41) at a magnification of 200×. Two areas of the respective tissue section were randomly selected and photographed, and pathological changes (such as the arrangement, distribution, and quantity of the chondrocytes) in the respective tissue section were assessed according to the Mankin scoring system described in Sahin K. et al. (2021), *Sci Rep,* 11, 14724, doi:10.1038/s41598-021-94142-3. The degrees of joint damage and recovery were scored on a scale from 0 to 6. The higher the scale, the higher the severity of OA is.

The data thus obtained were analyzed according to the method described in section 1 of "General Procedures".

Figure 6:
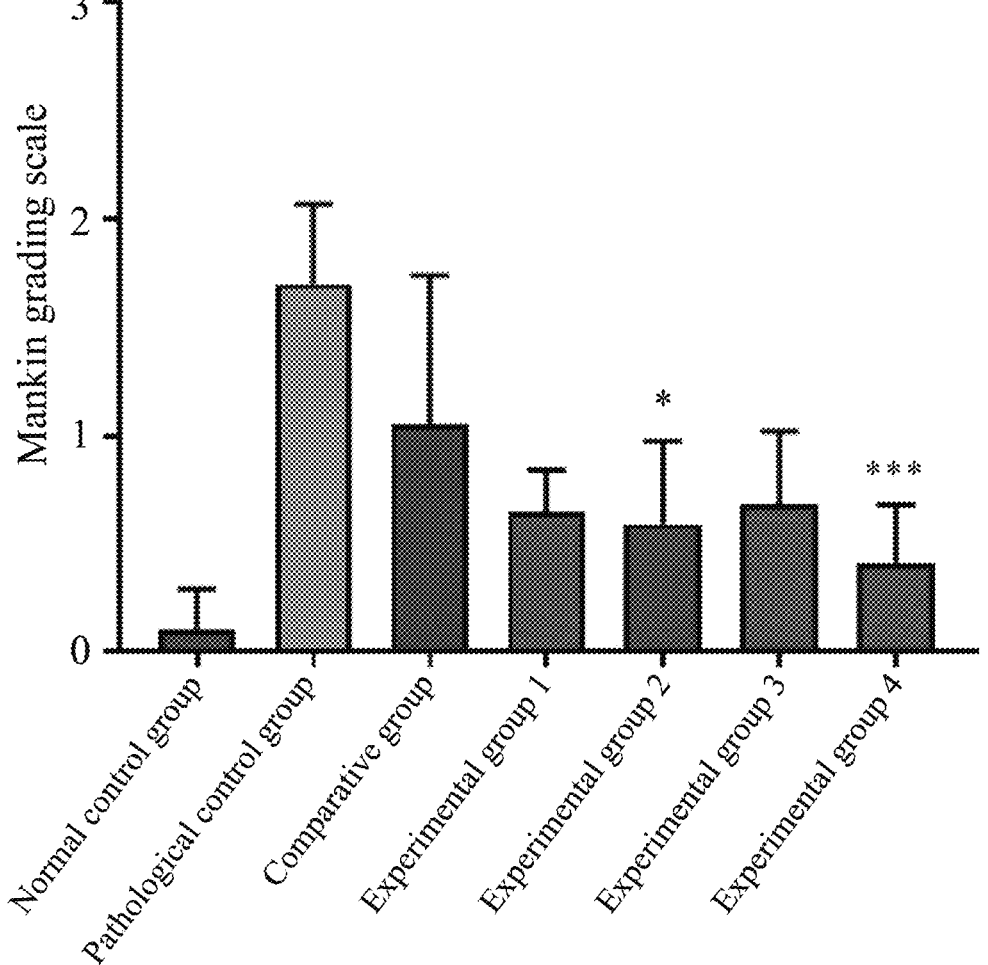
FIG. 6 shows the Mankin grading scale determined in each group of Example 4, infra, in which the symbols "*" and "***" respectively represent $p < 0.05$ and $p < 0.001$ (compared with the pathological control group).

FIG. 6 shows the Mankin grading scale determined in each group. As shown in FIG. 6, the Mankin grading scales determined in the experimental groups 1 to 4 were each significantly lower than that determined in the pathological control group. These results indicate that *Lactobacillus delbrueckii* subsp. *lactis* LDL557 of the present disclosure, whether in the form of live cells or dead cells, can effectively alleviate OA and articular cartilage lesions.

G. Safranin O and Fast Green Staining

The tissue section obtained in section E of this example was subjected to Safranin O and fast green staining using a staining protocol well-known to those skilled in the art, and was then observed under an optical microscope (Olympus, CKX41) at a magnification of 200×. Two areas of the respective tissue section were randomly selected and photographed, and pathological changes (i.e., cartilage damage) in the respective tissue section were assessed using the Osteoarthritis Research Society International (OARSI) classification system. The degrees of extracellular matrix (ECM) loss and recovery of the joint cartilage were scored on a scale from 0 to 24. The higher the scale, the higher the severity of OA is.

The data thus obtained were analyzed according to the method described in section 1 of "General Procedures".

Figure 7:
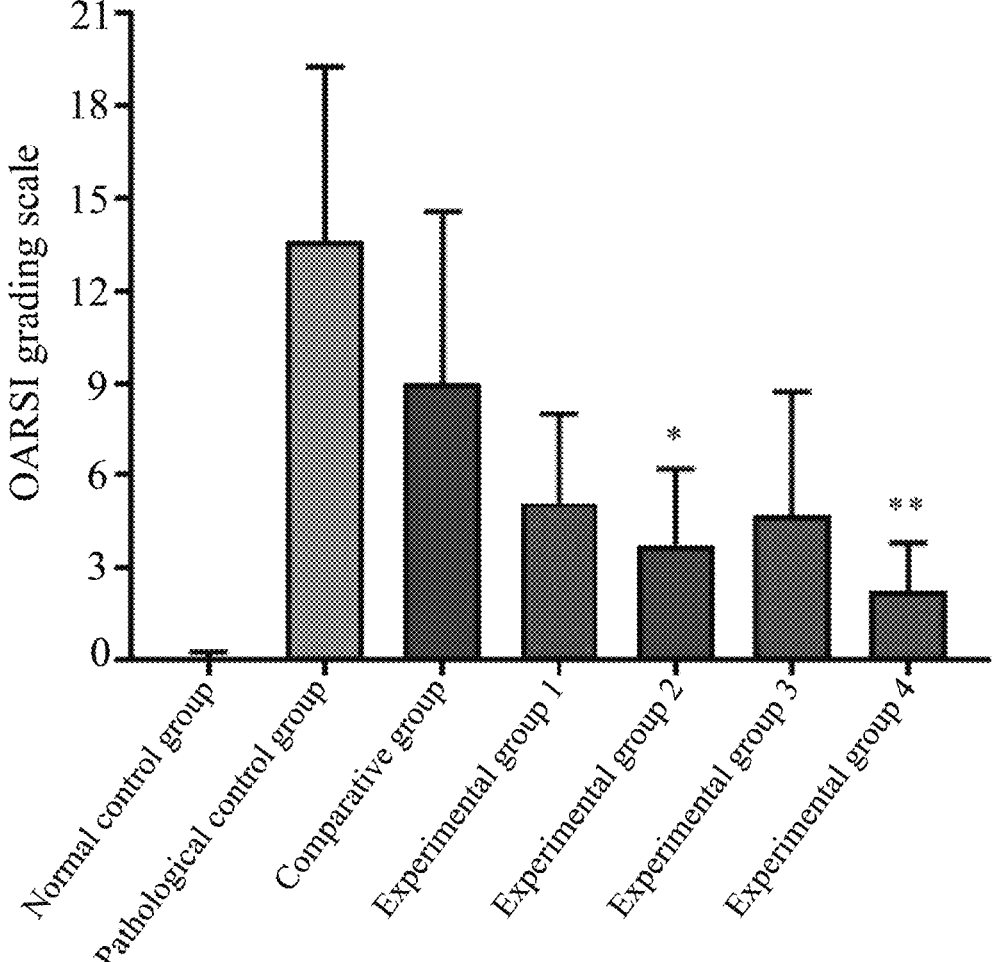
FIG. 7 shows the Osteoarthritis Research Society International (OARSI) grading scale determined in each group of Example 4, infra, in which the symbols "*" and "*" respectively represent $p < 0.05$ and $p < 0.01$ (compared with the pathological control group).

FIG. 7 shows the OARSI grading scale determined in each group. As shown in FIG. 7, the OARSI grading scales determined in the experimental groups 1 to 4 were each significantly lower than that determined in the pathological control group. These results indicate that *Lactobacillus delbrueckii* subsp. *lactis* LDL557 of the present disclosure, whether in the form of live cells or dead cells, can effectively prevent cartilage ECM loss and promote the recovery of articular cartilage, and hence can alleviate OA.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for alleviating osteoarthritis, comprising administering to a subject in need thereof a composition including an isolated strain of *Lactobacillus delbrueckii* subsp. *lactis* LDL557,
    wherein the isolated strain of *Lactobacillus delbrueckii* subsp. *lactis* LDL557 is deposited at Deutsche Sammlung von Mikroorganismen and Zellkulturen GmbH under an accession number DSM 33617.

2. The method as claimed in claim 1, wherein the composition is a food product or a pharmaceutical composition.

3. The method as claimed in claim 2, wherein the pharmaceutical composition is administered by a route selected from the group consisting of oral administration, parenteral administration, respiratory tract administration, and topical administration.

* * * * *